US007810494B2

(12) United States Patent
Harmer et al.

(10) Patent No.: US 7,810,494 B2
(45) Date of Patent: Oct. 12, 2010

(54) DRY POWDER INHALER

(75) Inventors: Quentin Harmer, Cambridge (GB); Roger William Clarke, Cambridge (GB); Stephen William Eason, Diss (GB)

(73) Assignee: Vectura Limited, Chippenham, Wiltshire (GB)

( * ) Notice: Subject to any disclaimer, the term of this patent is extended or adjusted under 35 U.S.C. 154(b) by 1106 days.

(21) Appl. No.: 10/571,725

(22) PCT Filed: Sep. 15, 2004

(86) PCT No.: PCT/GB2004/003940

§ 371 (c)(1),
(2), (4) Date: May 31, 2006

(87) PCT Pub. No.: WO2005/025656

PCT Pub. Date: Mar. 24, 2005

(65) Prior Publication Data

US 2007/0074721 A1 Apr. 5, 2007

(30) Foreign Application Priority Data

Sep. 15, 2003 (GB) ................................ 0321609.0

(51) Int. Cl.
*A61M 11/00* (2006.01)

(52) U.S. Cl. ........................... 128/203.21; 128/203.15; 128/203.12

(58) Field of Classification Search ............ 128/203.15, 128/203.12, 203.17, 203.16, 203.27, 206.28, 128/204.25, 204.24, 203.21; 604/58
See application file for complete search history.

(56) References Cited

U.S. PATENT DOCUMENTS

| | | | | |
|---|---|---|---|---|
| 2,534,636 | A | 12/1950 | Stirn | 128/206 |
| 4,338,931 | A | 7/1982 | Cavazza | 128/203.15 |
| 5,740,794 | A | 4/1998 | Smith et al. | 128/203.15 |
| 6,668,827 | B2 * | 12/2003 | Schuler et al. | 128/203.21 |
| 6,679,256 | B2 * | 1/2004 | Ingle et al. | 128/203.21 |
| 7,464,704 | B2 * | 12/2008 | Braithwaite | 128/200.21 |
| 2001/0029948 | A1 * | 10/2001 | Ingle et al. | 128/203.15 |
| 2002/0017297 | A1 * | 2/2002 | Burr et al. | 128/203.15 |
| 2003/0035777 | A1 * | 2/2003 | Patton et al. | 424/46 |

FOREIGN PATENT DOCUMENTS

| | | |
|---|---|---|
| DE | 3016127 | 11/1990 |
| DE | 20306808 | 7/2003 |
| EP | 0558879 | 5/1997 |

(Continued)

*Primary Examiner*—Steven O Douglas
(74) *Attorney, Agent, or Firm*—Davidson, Davidson & Kappel, LLC

(57) ABSTRACT

An Inhaler for delivering an aerosolized dose of a powdered drug for inhalation by a user is disclosed. The inhaler comprises a drug entrainment device vice to a receive a package having a piercable lid containing a dose to be delivered, the device including a drug outlet tube terminating with a primary piercing element to pierce an opening in said lid when a package is located in the inhaler, a secondary piercing member to pierce a plurality of peripheral openings in said lid and, an airflow path to enable the supply of a charge of gas into the package via said peripheral openings to scour the interior of a pierced package such that all or substantially all of the dose is entrained in the gas and flows out of the package via the drug outlet tube. A medicament pack is also disclosed.

20 Claims, 9 Drawing Sheets

FOREIGN PATENT DOCUMENTS

| | | |
|---|---|---|
| GB | 2340758 | 3/2000 |
| WO | 8901348 | 2/1989 |
| WO | 9958180 | 11/1999 |
| WO | 0187393 | 11/2001 |
| WO | 02053216 | 7/2002 |
| WO | 02089879 | 11/2002 |

* cited by examiner

DRY POWDER INHALER

FIELD OF THE INVENTION

The present invention relates to inhalers for the delivery of medicament in powdered form to the lung. The invention also relates to a medicament pack to contain a measured dose of a powdered medicament for use with a dry powder inhaler according to the invention.

BACKGROUND OF THE INVENTION

Traditionally, inhalers have been used to deliver medicament to the lung to treat local diseases of the lung such as asthma. However, when the inhaled particles are in the range 1 to 3 microns they can reach the deep lung area (alveoli) and cross into the bloodstream. This systemic delivery of pharmaceutically-active agents to the bloodstream via the lungs using an inhalation device has become a particularly attractive form of administering drugs to a patient many of whom are reluctant to receive drugs by injection using a needle. Furthermore, the administration of a drug using an inhaler may be carried out by a patient discreetly and in public without any of the known difficulties associated with injections involving a needle.

Although the repeatable dose of a powdered medicament emitted from a conventional dry powder inhaler may be relatively poor (the variation in respirable dose of known inhalers can be +/−20 to 30%), this is generally acceptable in the case of asthma drugs and the like. However, it will be appreciated that for the pulmonary delivery of systemic small molecule and protein and peptide drugs or for the administration of drugs such as insulin, growth hormone or morphine, this amount of variation in respirable dose is unacceptable. This is not only because it is considerably more important to ensure that the patient receives the same intended dose of these types of drugs each time the inhaler is used, so that a predictable and consistent therapeutic effect is achieved, but a relatively low respirable dose represents a significant wastage of what may be an expensive drug.

It will therefore be appreciated that for systemic pulmonary delivery, the provision of an inhalable aerosol requires an inhaler that can deliver the drug in a highly efficient, accurate and repeatable manner leading to a more predictable and consistent therapeutic effect which minimises any potentially harmful side effects for the patient as well as reducing the amount of costly drug required to deliver a therapeutic dose.

One important factor in maintaining the efficiency, accuracy and repeatability of the dose is to minimise the amount of drug that is retained in the inhaler mechanism and in the medicament pack in which the drug is stored prior to inhalation using the device. A conventional pack for an individual dose of dry powder medicament may include a gelatin capsule or a foil blister which is cold formed from a ductile foil laminate. A piercable foil laminate lid usually covers the blister which is heat sealed around the periphery of the blister. These types of package are preferred because each dose is protected from the ingress of water and penetration of gases such as oxygen in addition to being shielded from light and UV radiation and so offer excellent environmental protection. To administer a dose using a compressed gas powered inhaler, the capsule or foil lid is punctured by a piercing mechanism so that the drug can be entrained and carried to an aerosolising means, such as a nozzle, in a charge of gas which passes through the capsule or blister to the nozzle.

It will be appreciated that in an active inhaler of the aforementioned type, the same charge of gas provides the energy needed for both entraining the drug to evacuate the packaging and for aerosolising the drug once it has reached the nozzle. It is therefore important that the primary packaging does not present a significant restriction to the gas flow from the source of pressurised gas to the aerosolising nozzle. Bearing in mind that the amount of gas available for each dose is limited by what can be stored in a pressurised canister or generated in the device by the user by, for example, using a manually operated pump, the efficiency by which the drug is entrained in the airflow and so evacuated from its packaging must be as high as possible.

A problem with known inhalation devices in which the primary packaging for the drug is a conventional capsule or foil blister of the type referred to above is that it is possible for not all of the drug to be entrained in the airflow each time the device is used because the blister or capsule are typically pierced in such a way that the gas flowing into the blister through the pierced foil only partially scours the blister surfaces before flowing out of the blister. This problem is often exacerbated by the flap of foil cut by the piercing element as this can obscure parts of the blister from the flow of gas thereby restricting the free flow of gas throughout the entire volume of the blister and creating "dead" regions where gas flow is minimal or where secondary eddies form leading to powder becoming trapped. This trapped powder will have a significant detrimental effect on the repeatability and accuracy of the delivered dose as well as on the overall efficiency of the inhaler.

The efficiency of a dry powder inhaler may be measured in terms of the fine particle dose (FPD) or fine particle fraction (FPF). The FPD is the total mass of active agent which is emitted from the device following actuation which is present in an aerodynamic particle size smaller than a defined limit. This limit is generally taken to be 5 μm if not expressly stated as some alternative limit, such as 3μ or 1 μm, etc. The FPD is measured using an impactor or impinger, such as a twin stage impinger (TSI), multi-stage impinger (MSI), Andersen Cascade Impactor or a Next Generation Impactor (NGI). Each impactor or impinger has a pre-determined aerodynamic particle size collection cut points for each stage. The FPD value is obtained by interpretation of the stage-by-stage active agent recovery quantified by a validated quantitative wet chemical assay where either a simple stage cut is used to determine FPD or a more complex mathematical interpolation of the stage-by-stage deposition is used.

The FPF is normally defined as the FPD divided by the emitted or delivered dose which is the total mass of active agent that is emitted from the device following actuation and does not include powder deposited inside or on the surfaces of the device. The FPF may also, however, be defined as the FPD divided by the metered dose which is the total mass of active agent present in the metered form presented by the inhaler device in question. For example, the metered dose could be the mass of active agent present in a foil blister.

SUMMARY OF THE INVENTION

The present invention seeks to provide a dry powder inhaler in which all, or substantially all, of the internal surfaces of a pack containing a medicament dose are swept by the airflow so that substantially all of the drug is evacuated from the pack for delivery through an aerosolising nozzle and out of the device into the airway of a patient, thereby improving the delivered dose and hence the fine particle fraction of the delivered dose.

According to the invention, there is provided a dry powder inhaler for delivering a dose of medicament for inhalation by a user, the dose being contained in a medicament pack having a puncturable lid, the inhaler comprising a drug entrainment device including a drug outlet tube terminating with a primary piercing element to pierce an opening in said lid when a pack is located in the inhaler, a secondary piercing member to pierce a plurality of peripheral openings in said lid and, an airflow path to enable the supply of a charge of gas into the pack via said peripheral openings to scour the interior of a pierced pack such that substantially all of the dose is entrained in the gas and flows out of the pack via the drug outlet tube.

Preferably, the drug entrainment device includes an airflow inlet for the flow of air from the airflow path into a plenum chamber formed above the pierced lid of a pack, the inlet and the plenum chamber being configured such that a swirling airflow is generated in the plenum chamber.

In a preferred embodiment, the plenum chamber is substantially cylindrical in shape and the inlet intersects the curved wall of the chamber at a tangent thereto.

The secondary piercing member is configured to direct the swirling flow of air in the plenum chamber into the pack through the openings formed therein by the secondary piercing member. Advantageously, the secondary piercing member comprises a plurality of blades with a vane depending from each blade for piercing the lid of the pack and to direct the swirling airflow into the pack.

The aforementioned feature introduces swirl into the blister to improve the entrainment of the dose by ensuring that the surfaces of the blister are swept by the gas flow. The generation of swirl in the blister or capsule containing the drug also reduces the speed of delivery of the drug to the aerosolising nozzle and therefore assists in reducing the likelihood of deposition of drug in the aerosolising nozzle. The maximum loading of powder passing through the nozzle must be kept below a threshold otherwise the nozzle can become overloaded and its efficiency reduces. If the dose is introduced over a longer period of time, the powder density in the nozzle is kept sufficiently low and its efficiency is maintained.

Many drug formulations suitable for inhalation are highly cohesive and tend to adhere to the internal surfaces of the inhaler. Therefore, in addition to evacuating the primary packaging efficiently, it is also equally important to prevent deposition of the drug on the internal parts of the inhaler once it has been entrained in the airflow and whilst it travels through the aerosolising nozzle and mouthpiece into a users airway as this can also have a detrimental effect on the delivered dose. Furthermore, deposited drug may become detached during subsequent use of the inhaler resulting in an unpredictable variation in the delivered dose. Although this problem is partially alleviated because each dose is individually packaged so that any drug remaining in a used primary package is removed and disposed of together with that primary package and so cannot have any effect on the delivered dose during subsequent uses of the inhaler, any residual drug remaining in unwiped or unaccessible parts of the inhaler can still have an appreciable effect on the delivered dose and in subsequent uses of the inhaler. Although the passage from the primary packaging to the nozzle does not present a significant restriction to the gas flow and hence regions where deposition may easily occur, the aerosolising nozzle is particularly susceptible to deposition as the medicament entrained in the airflow enters the nozzle at high speed and over a very short period of time resulting in a proportion of the powdered medicament adhering to the walls of the nozzle.

The present invention also seeks to overcome or substantially alleviate the aforementioned problem caused by residual drug remaining in the nozzle and in the flow path between the primary package and the nozzle during subsequent inhalations which can have a detrimental effect on the delivered dose of medicament and the fine particle fraction of the delivered dose.

According to another aspect of the invention there is provided a medicament pack for use in an inhalation device comprising a drug storage chamber to contain a single dose of medicament and an aerosolising nozzle for generating an inhalable aerosol of the dose for inhalation by a user when a charge of gas is passed through the pack. Preferably the pack, incorporating both the drug storage chamber and the nozzle is disposed of after the drug has been discharged therefrom and is not re-filled.

In a preferred embodiment, the drug storage chamber and the aerosolising nozzle are integrally formed into a single module.

In one embodiment, the medicament pack comprises a blister having two compartments forming the drug storage chamber and the aerosolising nozzle respectively, each compartment being sealed with a piercable lid to enable an inhaler to pierce an inlet for the gas in the dose storage chamber and an outlet for the aerosolised dose in the aerosolising nozzle.

Preferably, an integral drug feed path communicates the drug storage chamber with the aerosolising nozzle.

In another embodiment, the drug storage compartment and the aerosolising nozzle are integrally formed from a moulded plastics material which is sealed with a piercable lid to enable an inhaler to pierce an inlet for the flow of gas into the dose storage chamber and an outlet for aerosolised dose in the aerosolising nozzle.

Alternatively, the drug storage compartment and the aerosolising nozzle are integrally formed from a moulded plastics material which is sealed with a piercable lid to enable an inhaler to pierce an inlet for the flow of gas into the drug storage chamber, an aperture being formed in the moulded plastic to form an outlet for the dose from the aerosolising nozzle.

In another embodiment, the medicament pack comprises a sheet in which is formed a plurality of drug storage chamber and nozzle pairs. Alternatively, a single nozzle and a plurality of drug storage chambers can be formed in the sheet, a drug feed path connecting each of the drug storage chambers with the nozzle.

In a preferred embodiment, the nozzle is a substantially cylindrical vortex chamber. The inlet from the drug feed tube intersects the chamber at a tangent and the outlet is coaxial with the longitudinal axis of the cylinder. The cylinder may be provided with a frustoconical portion in the region of the outlet for directing the airflow within the chamber towards the outlet.

BRIEF DESCRIPTION OF DRAWINGS

Embodiments of the invention will now be described, by way of example only, with reference to FIGS. 2 to 11 of the accompanying drawings, in which.

DETAILED DESCRIPTION OF THE INVENTION

Figure 1:
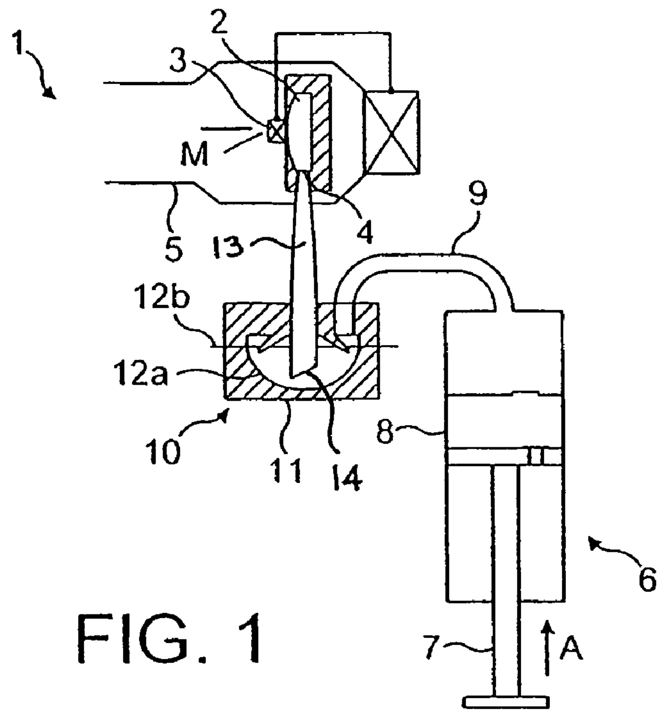
FIG. 1 represents a schematic diagram of a conventional pressurised gas powered active dry powder inhaler.

Referring now to the prior art drawing of FIG. 1, a pressurised gas powered active dry powder inhaler 1 for aerosolising a powdered medicament for inhalation by a user is shown. The inhaler 1 comprises a vortex chamber or nozzle 2 having an exit port 3 and an inlet port 4 for generating an aerosol of medicament M. The nozzle 2 is located within a mouthpiece 5 through which a user inhales the aerosolised medicament M.

The powdered medicament or drug M is supplied to the nozzle 2 in a gas or airflow generated by a pump represented in FIG. 1 as a piston pump 6 comprising a plunger 7 received in a pump cylinder 8 and a reservoir fluidly connected to the pump via a non-return valve. An airflow path 9 extends from the pump cylinder 8 to a drug entrainment device 10 disposed above a housing 11 to support a foil blister 12 containing a single dose of medicament (typically between 0.5 and 5 mg). The blister 12 has a cold formed foil blister base 12*a* sealed with a hard rolled foil laminate lid 12*b* chosen to facilitate piercing. A drug feed tube 13 extends from the inlet port 4 of the nozzle 2 and into the housing 11 where it terminates in a piercing element 14. When the inhaler 1 is to be used, the reservoir is primed with a charge of compressed air by sliding the plunger 7 into the pump cylinder 8 (in the direction of arrow "A" in FIG. 1) to compress the air contained therein. Thereafter, the housing 11 and the drug feed tube 13 are moved relative to each other to cause the piercing element 14 to break the foil laminate layer 12*b* and penetrate into the blister 12 so that when the user inhales through the mouthpiece, a valve, which may be breath actuated, releases the charge of compressed air from the reservoir so that it flows along the airflow path 9 through the blister 12 where it entrains the medicament contained therein. The airflow together with the entrained drug flows up through the drug feed tube 13 and into the nozzle 2 via the inlet 4 where a rotating vortex of medicament and air is created between the inlet and outlet ports 4,3. As the medicament passes through the nozzle 2, it is aerosolised by the high turbulent shear forces present in the boundary layer adjacent thereto as well as by the high level of turbulence in the vortex chamber and through collisions between agglomerates and other agglomerates and between agglomerates and the walls of the nozzle. The aerosolised particles exit the nozzle 2 via the exit port 3 and are inhaled by the user through the mouthpiece 5.

Improved Evacuation of a Dose of Medicament from a Blister

Figure 2:
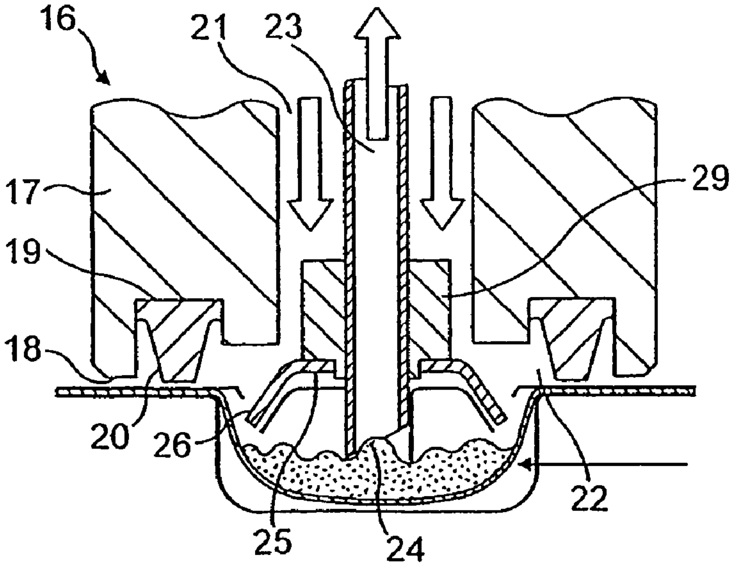
FIG. 2 shows a cross-sectional side elevation of a portion of a drug entrainment device according to the invention, after piercing of a blister has taken place, for use in the pressurised gas powered inhaler of FIG. 1.

FIG. 2 illustrates part of a drug entrainment device 16 suitable for use with the conventional dry powder inhaler 1 illustrated in FIG. 1. The drug entrainment device 16 improves access to the medicament contained in a blister 12 and ensures that its internal surface is swept and scoured by the airflow so that all or substantially all of the medicament (at least 95%) is entrained in the airflow and carried to the aerosolising nozzle thereby increasing the delivered dose and reducing the respirable dose variation between successive uses of the inhaler.

Prior to use, the blister 12 is inserted into the housing 11 within the inhaler 1 so that its piercable lid 12*b* is located below the drug entrainment device 16. The drug entrainment device 16 comprises a body 17 having a lower end 18 in which is formed a channel 19 to receive a sealing member 20 which makes contact with the blister 12 around the periphery of the laminate lid 12*b* so as to form a fluid tight seal therewith. An annular conduit 21 extends through the drug entrainment device 16 via a plurality of holes which join and widen at their lower end 18 in the vicinity of the sealing member 20 so as to form a plenum chamber 22 above the blister lid 12*b* when the sealing member 19 is in sealing engagement with the periphery thereof. The opposite unillustrated end of the annular conduit 21 is connected via a valve to a source of pressurised gas such as a piston pump 6 as described with reference to FIG. 1. A central drug feed tube 23 extends axially through the annular conduit 21 and protrudes beyond the lower end 18 and the sealing member 20 and terminates in an angled face to form a central piercing element 24 for cutting the lid 12*b* of the blister 12. A secondary peripheral piercing member 25 is mounted on the central drug feed tube 23 adjacent to the angled end forming the central piercing element 24 for making multiple additional piercings in the surface of the blister lid 12*b* for reasons that will become apparent. The opposite end of the drug feed tube 25 is in communication with an aerosolising nozzle such as the nozzle 2 described with reference to the inhaler of FIG. 1.

Figure 3:
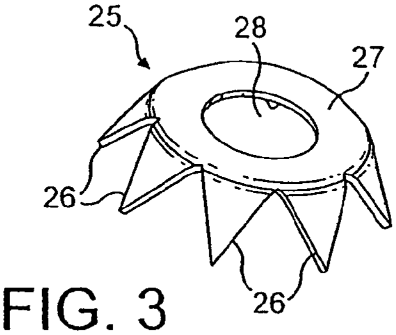
FIG. 3 illustrates a perspective view of the secondary piercing element used in the drug entrainment device shown in FIG. 2.

A perspective view of the secondary piercing member 25 is shown in FIG. 3 from which it will be appreciated that it comprises a star shaped ring incorporating a plurality of peripheral pointed piercing elements 26 which are deflected or angled out of the plane of the body 27 of the ring. In the illustrated embodiment, there are eight pointed piercing elements 26. However, it has been found that the improved drug entrainment provided by the invention is achieved with 4 piercing elements 26, although 8 piercing elements 26 have been found to provide the most significant advantages. An aperture 28 in the centre of the body 27 is dimensioned so as to engage with a mounting member 29 fixedly attached to the lower end of the outer surface of the drug feed tube 23 so that the pointed piercing elements 26 point in the same direction as the central piercing element 24 and towards the lid 12*b* of a blister 12 mounted in the housing 11 prior to use.

The secondary piercing member 25 is preferably manufactured by chemical milling from stainless steel sheet and subsequent pressing. A further advantageous embodiment for high volume manufacture is to integrate the primary and secondary piercing members 24,25 in a single injection moulded part. Possible materials include Polyetheretherketone (PEEK), liquid crystal polymer (LCP), Polyamide, Polysulphone (PS) Polyetherimide (PEI), Polyphenylsulphone (PPS) thermosetting plastics.

When the device is used, a blister 12 is inserted into the housing 11 and is brought up to meet the drug entrainment device 16 such that the central piercing element 24 and each of the secondary piercing elements 26 pierce the foil lid **12*b* and thereby create a pattern of openings in the surface of the blister 12*b*. When the valve (not shown) between the source of compressed air and the annular conduit 21 is opened, possibly in response to the user's inhalation, a charge of pressurised gas flows down through the annular conduit 21 and into the plenum chamber 22 and from there through the multiple piercings in the lid 12*b* formed by the secondary piercing elements 26 into the blister 12 so that the medicament is entrained in the airflow and flows up the drug feed tube 23** to the aerosolising nozzle.

It has been found that by using the aforementioned combination of central piercing element 24 and secondary peripheral piercing elements 26, the airflow through the blister is significantly improved so that nearly all of the medicament is entrained and evacuated from the blister 12 without any powder becoming trapped in spaces that have not been swept or scoured by the airflow. As a result, the delivered dose of medicament is improved, as is the fine particle fraction of total dose. It will be appreciated that the secondary piercing elements 26 create a smoothly controlled and predictable cut as the tip of each secondary piercing element 26 first creates a hole in the foil laminate **12*a* and "pushes" the cut foil flap out of the way. This should be contrasted with conventional pin type piercing elements which effectively burst through and tear the foil laminate forming unpredictable cut edges and flaps which can have a detrimental effect on the airflow through the blister 12. Furthermore, the secondary piercing elements 26 act as baffles to prevent the airflow entering the blister 12 from passing straight through it from the openings made by the secondary piercing elements 26 to the outlet feed tube 23**. It should also be noted that the charge of compressed gas flows directly into and through the blister rather than being used to induce a secondary flow of air through the blister. By allowing the charge of compressed gas to pass directly through the blister entrainment of the medicament is significantly more efficient.

The inventors have also found that a number of factors have a significant influence on the amount of drug that is consistently evacuated from the blister during repeated use of the device. In particular, the shape, angle number and configuration of the secondary piercing elements 26 has a significant effect on the airflow through the blister 12, as does the diameter of the outlet feed tube 23 and its depth of penetration into the blister 12. To explain these factors in more detail, reference will be made to FIG. 4 and Tables 1 to 3.

A number of tests were conducted. These tests were part of a fractional factorial design experiment in which 10 variables were evaluated. A 3 mg dose of pure micronised Sodium Cromoglycate was used with a reservoir of 15 ml of air at a pressure of 1.5 bar gauge. The dose was contained in a foil blister of the type described and having the dimensions referred to in Table 3 with reference to FIG. 4. All the variables together with the preferred ranges, most preferred ranges and preferred values are shown in Table 3 which should be considered in conjunction with the drawing of FIG. 3.

Considering first the drug feed tube 23, Table 1 shows the results of evacuation from the blister 12 using a drug feed tube 23 having a first internal diameter ("d" in FIG. 4) of 1.50 mm and another drug feed tube 23 having a second internal diameter "d" of 1.22 mm. It can be ascertained from Table 1 that both the average evacuation and the repeatability of evacuation are better with a 1.22 mm diameter outlet tube than with a 1.5 mm diameter feed tube 23. As can be seen from Table 3, it was found that 1.22 mm was the most preferred value for the internal diameter of the drug feed tube 23.

TABLE 1

Blister evacuation with different outlet tube diameters.

| | Average evacuation over four sets of 10 tests | Average standard deviation of evacuation for four sets of 10 tests. |
|---|---|---|
| Outlet tube internal diameter (d) = 1.50 mm | 80.0 | 7.5 |
| Outlet tube internal diameter (d) = 1.22 mm | 96.4 | 2.0 |

Referring now to Table 2, this shows the effect on the evacuation from a blister 12 when the distance by which the drug feed tube 23 protrudes into the blister 12 ("b" in FIG. 4) is altered. In the first test, the drug feed tube 23 is positioned so as to protrude into blister 12 by 2.1 mm and in a second test, the drug feed tube 23 is allowed to protrude into the blister 12 by a distance of 2.4 mm. The results show that evacuation from the blister 12 is improved if the drug feed tube 23 protrudes less far into the blister 12. As can be seen from Table 3, it was found that 1.6 mm was the most preferred value for the depth of penetration of the drug feed tube 23 into the blister 12. However, it was found that penetration depths in the range 1.5 to 2.7 mm produced satisfactory results although a range of between 1.5 to 1.9 mm is largely preferred.

TABLE 2

Blister evacuation when the protrusion of the outlet tube is at two different settings.

| | Average % evacuation over four sets of 10 tests | Average standard deviation of evacuation for four sets of 10 tests. |
|---|---|---|
| Protrusion of outlet tube into blister (b) = 2.1 mm | 96.7 | 1.9 |
| Protrusion of outlet tube into blister (b) = 2.4 mm | 79.6 | 7.6 |

The evacuation quoted in FIGS. 6 to 9 was measured as follows: Sodium Cromoglycate was weighed into an empty foil blister using a five figure balance and the fill weight recorded. The blister was then tested in an Aspirair device (described in the Applicant's earlier published PCT application No. WO 01/00262) delivering a reservoir of 10 ml of air at a pressure of 1.5 bar. The blister was then re-weighed and the new weight recorded (as evacuated weight). The evacuation efficiency of the entrainment device was calculated using the following formula:

$$\text{Evacuation} = \frac{\text{Fill Weight} - \text{Evacuated Weight}}{\text{Fill Weight}} \times 100$$

As mentioned above, Table 3 lists all the additional factors that affect the evacuation of the drug from the blister 12 with particular reference to the dimensions and shape of the secondary piercing elements 26.

TABLE 3

Preferred dimensions for the secondary piercing member of FIG. 3.

| Feature | Preferred range | Most preferred range | Most preferred value |
|---|---|---|---|
| Inscribing diameter, D of the secondary piercing elements | 4-9 mm | 5-7 mm | 6.8 mm |
| Height of secondary piercing member, H | 1.2-2.0 mm | 1.4-1.8 mm | 1.6 mm |
| Internal diameter, d, of the outlet tube | 1.0-1.5 mm | 1.20-1.30 mm | 1.22 mm |
| Number of secondary piercing elements | 4-10 | 6-8 | 8 |
| Protrusion, a, of the secondary piercing member into the blister | 0.9-2.0 mm | 1.1-1.5 mm | 1.20 mm |
| Protrusion, b, of the outlet tube into the blister | 1.5-2.7 mm | 1.5-1.9 mm | 1.6 mm |
| Angle, α, of the face of the outlet tube to its axis | 30-70 degrees | 45-70 degrees | 60 degrees |
| Angle, β, of the secondary piercing elements to the axis of piercing | 30-60 degrees | 25-45 degrees | 40 degrees |
| Blister diameter, C | 4-12 mm | 6-9 mm | 8.0 mm |
| Blister depth, e | 2.0-3.50 mm | 2.5-3.0 mm | 2.8 mm |

The preferred dimensions for the secondary piercing member 25 have been selected for evacuation from a circular blister 12 having a diameter of 8 mm and a depth of 2.8 mm. This size of blister 12 is sufficient to carry a dose of up to 5 mg of typical inhalable medicaments and provides a headspace in the blister 12 to facilitate straightforward loading of the drug into the blister 12 in high volume production. A preferred number of secondary piercing elements 26 on the secondary piercing member 25 is eight. In order to create an even airflow around the periphery of the blister 12 it is desirable to provide a large number of piercings therein. However, it is also necessary to open up a sufficient area of the foil lid 12*b* to allow free flow of the air through the blister 12. With many piercings in a given size of blister 12 either the holes have to become smaller or they have to be pierced so close to each other that the foil 12*b* between them is likely to tear during piercing. Eight secondary piercing elements 26 can easily be accommodated within the circumference of the blister 12 whilst still allowing each secondary piercing element 26 to open up a sufficient area of flow into the blister 12. A larger blister 12 may allow a secondary piercing member 25 with more piercing elements 26 to be used and a smaller blister 12 would allow fewer.

Figure 4:
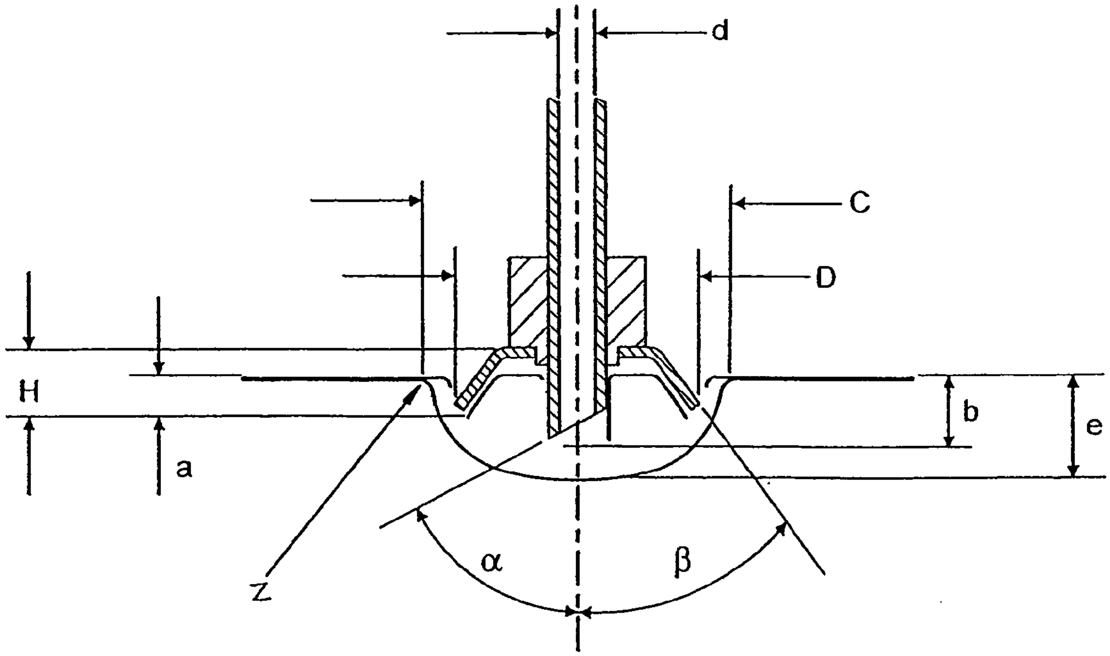
FIG. 4 shows a cross-sectional side elevation of a portion of the drug entrainment device of FIG. 2.

To facilitate even evacuation of the powder from the blister 12, the drug outlet tube 23 would ideally have a flat end (i.e. α=90 degrees). However, the tube 23 must also pierce a controlled cut into the lid 12*b* of the blister 12 and fully open a flap so that the powder exit is not impeded. If the angle α is close to 90 degrees a higher force is required to pierce the foil lid 12*b* and the drug feed tube 23 pierces the lid 12*b* in an uncontrolled manner. An angle of 60 degrees creates a controlled and repeatable cut in the foil 12*b* without unduly increasing the piercing force. The angle β influences how much pierced area is opened up to the airflow when the lid 12*b* is pierced. An angle close to 45 degrees is desirable to gain the greatest open area when fully pierced, as shown in FIG. 4. For a given length from the root to the tip of the primary piercing element 24, l, the greatest open area for flow is given when l cos β sin β is maximised. This occurs when β=45 degrees. A slightly lower value has been chosen (40 degrees) in the preferred embodiment, to make the piercing process more tolerant of variations in piercing depth due to tolerance variations from device to device.

The dimensions that have the most significant influence on performance are the depths of the secondary piercing member 25 and the outlet tube 23 in the pierced position. If the pierced area is too small, the airflow resistance of the blister increases and the evacuation of powder from the blister is reduced. The preferred ranges for the secondary piercing member 25 are chosen to open as much pierced area in the top of the blister as possible without the piercing elements 26 touching the blister base 12*a* or punching a contiguous ring through the lid 12*b*. The preferred ranges for the outlet tube 23 are chosen such that the tube 23 fully cuts and opens a flap in the lid 12*b* but does not go too close to the base 12*a* of the blister 12. In order to fully open a flap, the tube 23 must pierce a full diameter hole therein. (i.e. pierce to a depth below the lid 12*b* of >OD/tan α where OD is the outer diameter of the outlet tube 23 and α is as shown in FIG. 4). If the tube 23 is close to the base 12*a* of the blister 12, the flow of powder from the blister 12 up the tube 23 is impeded and evacuation of powder is reduced. The point of the primary piercing element 24 of the outlet tube 23 should be 0.2 mm and preferably greater than 0.5 mm from the base 12*a* of the blister 12.

Figure 5:
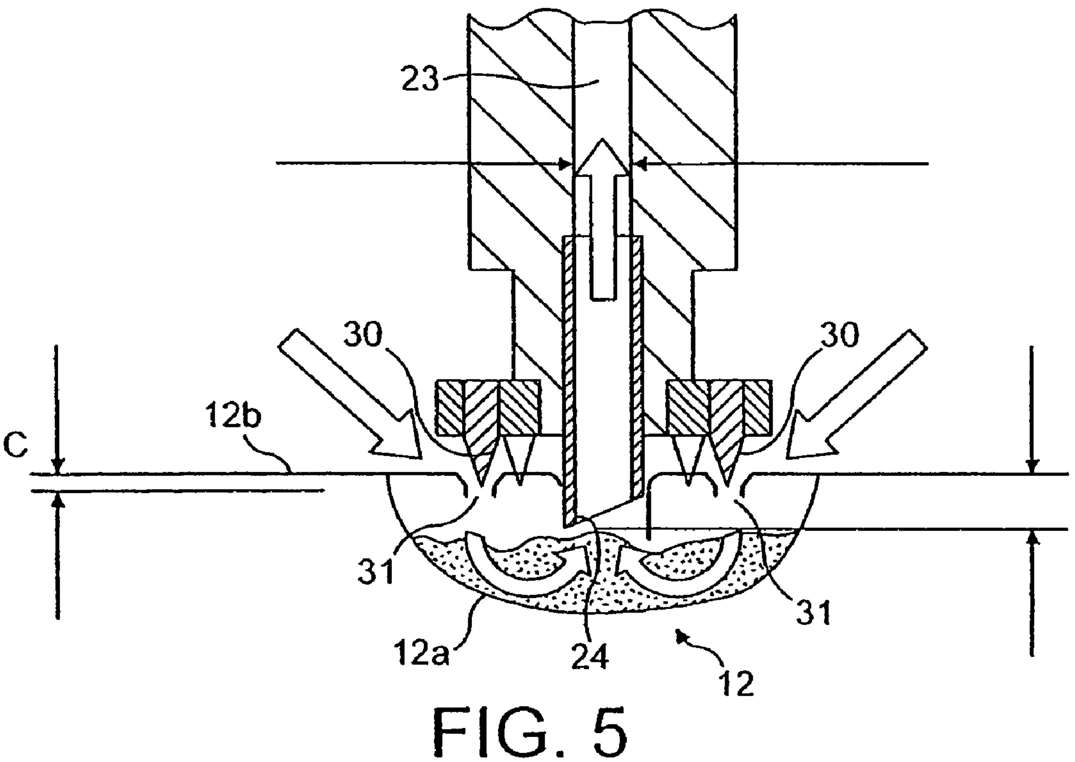
FIG. 5 illustrates an alternative embodiment of the drug entrainment device shown in FIG. 2.

An alternative embodiment of drug entrainment device which also promotes efficient evacuation from a foil blister 12 is illustrated in FIG. 5. In this configuration, the secondary piercing member 25 is replaced by a plurality of solid pointed piercing pins 30 arranged around the central drug feed tube 23. In use, the drug entrainment device 16 pierces the lid 12*b* and the blister 12 is then retracted by a small distance indicated by "C" in the Figure. Retraction of the blister 12 moves the pins 30 out of the apertures they have created to allow access to the interior of the blister 12 by the air flow passing down through the annular conduit 21. In practice, the retraction mechanism would ideally comprise a cam arrangement associated with the blister 12 that causes the blister 12 to withdraw by a small distance once the lid 12*b* has been pierced. In this way, a number of peripheral inlet holes 31 are formed in the lid 12*b* of the blister 12 together with the central hole formed by the central piercing element 24.

Table 4 is a table comparing the performance of the second embodiment with that of the first embodiment. In these tests, the first embodiment provides improved evacuation from the blister, improved delivered dose and improved fine particle fraction of total dose. Furthermore, the first embodiment is preferred because no retraction mechanism is then required making the device simple to manufacture and operate. However, the performance of the drug entrainment device with retractable pins or retractable blister is also an improvement over known configurations.

TABLE 4

Blister evacuation and inhaler performance of the retracting drug entrainment device and the non-retracting drug entrainment device

| Each result average of two MSLI tests | Delivered dose as % of total dose | FP dose as % of total dose | % evacuation from the blister |
|---|---|---|---|
| Retracting pierce head | 92.2% | 69.2% | 97.7% |
| Non-retracting piercing star | 93.7% | 71.9% | 99.6% |

In addition to altering the pattern and configuration of air inlets into and out of the blister 12, it has also been found that drug entrainment can be significantly improved by altering the shape of the secondary piercing member 25 to enhance the creation of a swirling airflow within the blister 12. Evacuation of the medicament from the blister 12 is thereby improved by ensuring that the internal surface thereof is completely swept by the gas flow.

Reference will now be made to the drawing of FIGS. 6A, 6B and 6C which illustrates a top plan view and two side elevational views of another embodiment of secondary piercing member 35 which would take the place of the secondary piercing member 25 mounted on the central feed tube 23 in the embodiment of FIG. 2. As can be seen, the secondary piercing member 35 now comprises a ring having a plurality of arms or blades 36 extending from a central aperture 37 in opposite directions (four being shown in the embodiment of FIG. 6) such that they extend substantially at right angles to the axis of the central feed tube 23 when the secondary piercing member 35 is mounted on the central feed tube 23 so that the central feed tube 23 extends through the aperture 37. On the side of the end of each arm 36 remote from the aperture 37, a flap is formed having an arcuately shaped outer periphery 38. Each flap is angled downwardly out of the plane of the arms 36 to form a vane surface 39 which is used to pierce the foil lid 12*b*. The vane surface 39 also serves to induce a swirling motion to the charge of compressed gas passing down through the annular conduit 21 and as it flows from the annular conduit 21 through the plenum chamber 22 and into the blister 12 via the openings therein created by the vanes 39 so as to cause the air to circulate around the blister 12 substantially around the axis of the central feed tube 23.

Figure 6A:
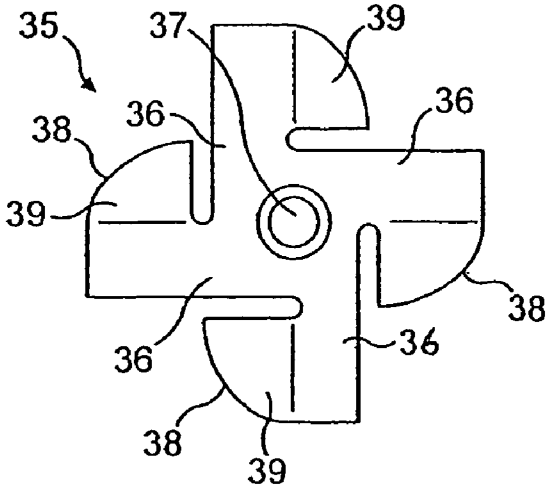
FIGS. 6A, 6B and 6C illustrate top plan and side views respectively, of an alternative version of secondary piercing element which serves to impart a swirling motion to the airflow as it passes into and through the blister.
Figure 6B:
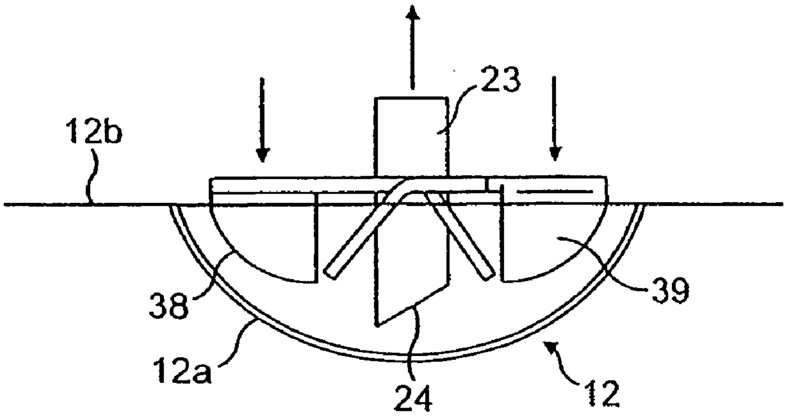

Although FIG. 6B shows the secondary piercing element 35 with the vanes almost entirely received within the blister 12, it will be appreciated that a proportion of the vane surfaces 39 may remain above and outside of the blister 12 so as to induce a swirling motion to the airflow within the plenum chamber 22 before it passes into the blister 12 through the apertures formed in the blister 12 by the vanes 39.

Figure 7A:
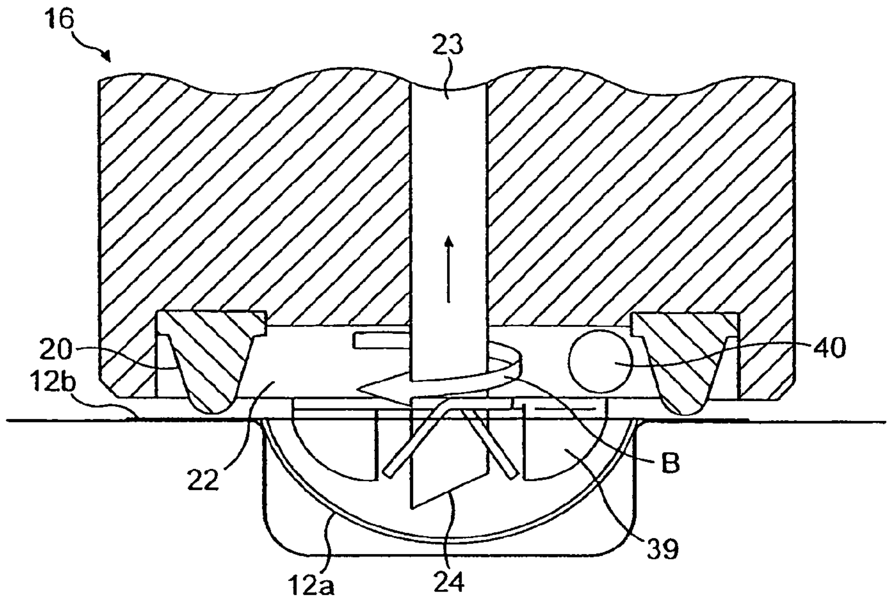
FIGS. 7A and 7B illustrate two cross-sectional side elevations of a modified version of the drug entrainment device shown in FIG. 2, using the secondary piercing element of FIGS. 6A and 6B.
Figure 7B:
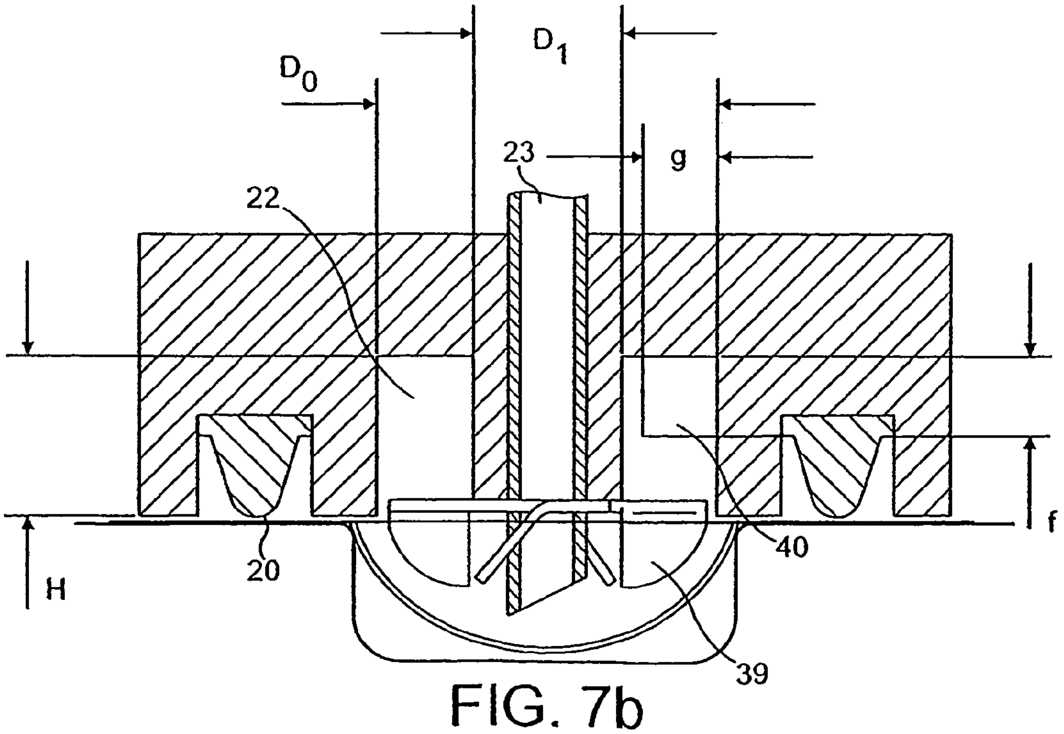

In a modified and preferred version of the aforementioned embodiment, as illustrated in FIGS. 7A and 7B, a swirling motion, indicated by arrow "B", may be generated in the plenum chamber 22 above the blister 12 and secondary piercing member 35 by introducing some or all of the charge of compressed air into the plenum chamber 22 via a tangential gas inlet 40 rather than via the annular airflow conduit 21. In this case, the vanes 39 serve to maintain the swirling airflow generated in the plenum chamber as the air enters the blister. Without the vanes, a substantial portion of the swirling effect is lost as the air enters the blister and so the combination of the vanes and tangential flow inlet 40 prevent "straightening out" of the flow as it enters the blister 12.

Figure 6C:
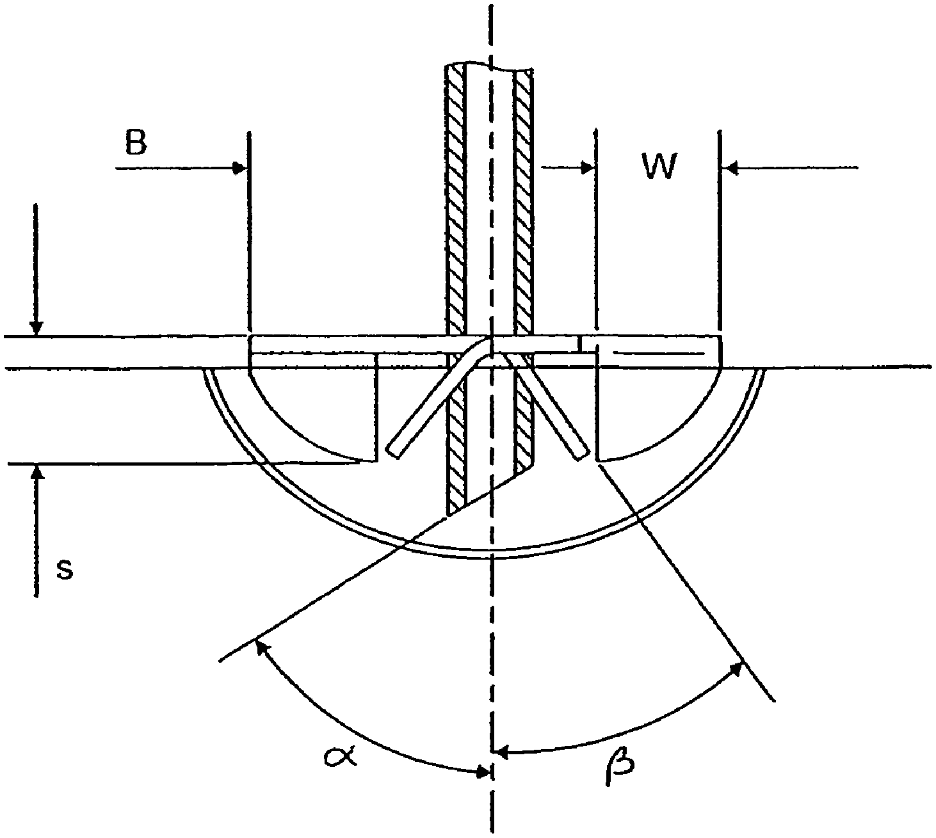

The preferred dimensions and angles referred to on FIGS. 6C and 7B are shown in Table 5. The size of the star, or secondary piercing member, is related to the size of the blister. In a preferred embodiment, the blister diameter is 8 mm and its depth 2.8 mm. If a different sized blister were to be employed, the piercing star would be scaled accordingly. The vanes of the secondary piercing element have two functions: to open up a sufficiently large piercing to allow air flow and to promote, or at least not diminish, swirl in the air as it enters the blister. Accordingly, their size is chosen to be as large as can practicably be accommodated by the blister. The vane profile is chosen to match the curved profile of the blister bowl although they do not touch the sides of the blister when in the pierced position. The angle of the vanes is chosen to be close to 45° to the foil to open up the largest possible flow area for a given size of vane. In the preferred embodiment, four vanes are used. In an ideal case a large number of vanes would allow swirling flow to enter the blister uniformly at all points around the periphery of the blister. However, piercing at many points can cause the foil to tear in an uncontrolled and therefore undesirable manner. Four vanes provide a controlled pierce and allow sufficient airflow into the blister. A larger blister might allow more vanes and a small blister would accommodate fewer. The dimensions of the plenum chamber 22 are chosen to create a strongly swirling airflow above the blister that will be transmitted to the dose therein. The inlet is sized to present a minimal resistance to the airflow compared with the resistance of the vortex nozzle downstream of the blister. The remaining dimensions such as the internal diameter (d) of the drug feed tube 23, the depth of penetration (b) of the drug outlet tube 23 into the blister, the angle (α) of the face of the outlet tube 23 to its axis, the blister diameter (C) and, the blister depth (e) are all the same as those shown in Table 3.

TABLE 5

Preferred dimensions for the secondary piercing element and plenum chamber of FIGS. 6 and 7.

| Feature | Preferred range | Most preferred range | Most preferred value |
|---|---|---|---|
| Span, B of the secondary piercing element | 4-9 mm | 6-7.5 mm | 7.2 mm |

TABLE 5-continued

| Preferred dimensions for the secondary piercing element and plenum chamber of FIGS. 6 and 7. | | | |
|---|---|---|---|
| Feature | Preferred range | Most preferred range | Most preferred value |
| Height of the secondary piercing element, s | 1.2-2.0 mm | 1.4-1.8 mm | 1.6 mm |
| Width, w of piercing vanes | 1-3 mm | | 1.7 mm |
| Number of secondary piercing elements | 2-8 | | 4 |
| Angle, β, of the piercing vanes to the axis of piercing | 30-60 degrees | 35-55 degrees | 45 degrees |
| Plenum diameter, $D_O$ | 5-8 mm | | 6.8 mm |
| Plenum inner diameter, $D_I$ | 1.6-5 mm | | 3.8 mm |
| Plenum height, H | 1-5 mm | | 3.75 mm |
| Plenum inlet height, f | 30-100% of plenum height | | 1.5 mm |
| Plenum inlet projected width, g | 50 -100% of $(D_O - D_I)/2$ | | 1.5 mm |

As already mentioned, the introduction of a swirling airflow into the blister 12 increases the amount of medicament that is entrained in the airflow and evacuated from the blister 12 through the drug feed tube 23 to the aerosolising nozzle 2 and so the delivered dose and fine particle fraction of delivered dose is improved.

In addition to the foregoing, it is not always possible to ensure that the inhaler is used in the correct orientation by the user. It is therefore important that performance is not adversely affected for example when the inhaler is used upside down. A key benefit of introducing swirl to the powder in the blister is that the evacuation is less affected by the orientation of the inhaler.

Table 6, below, shows the results of tests with the inhaler device held upside down during piercing of the blister. Foil blisters were filled with 3 mg of Sodium Cromoglycate and then tested in a device with a reservoir volume of 15 ml and a reservoir gauge pressure of 1.5 bar. The emitted dose was measured using a DUSA apparatus and wet chemical assay to evaluate the quantity of drug. Five consecutive shots were evaluated in this way and the mean and RSD (=standard deviation/mean) calculated.

With the standard plenum and secondary piercing element of FIGS. 2 and 4, the emitted dose drops by 9 percentage points when the blister is pierced upside down. The dose to dose variation over five shots is also significantly worse when pierced upside down with the RSD increasing from 2% to 10%. With the tangential airflow inlet to the plenum chamber 22 and the secondary piercing element of FIGS. 6 and 7, the mean emitted dose is improved and the change in performance when piercing the blister upside down is reduced to 3 percentage points. Importantly, the dose to dose variation over five shots is the same whether the blister is pierced upside down or in the correct orientation. This is a significant benefit over the standard arrangement because the swirl arrangement will be able to achieve more consistent dosing regardless of the orientation of use.

TABLE 6

| Effect of inhaler orientation with standard piercing arrangement and swirl generating piercing arrangement | | | |
|---|---|---|---|
| Standard piercing arrangement (secondary piercing element and inlet to plenum as in FIG. 2) | | Swirling flow in the blister (secondary piercing element of FIGS. 6 and tangential inlet to plenum of FIG. 7) | |
| Correct pierce orientation | Pierced upside down | Correct pierce orientation | Pierced upside down |
| Mean ED: 86%<br>RSD: 2% | Mean ED: 77%<br>RSD: 10% | Mean ED: 96%<br>RSD: 2% | Mean ED: 93%<br>RSD: 2% |

Figure 11:
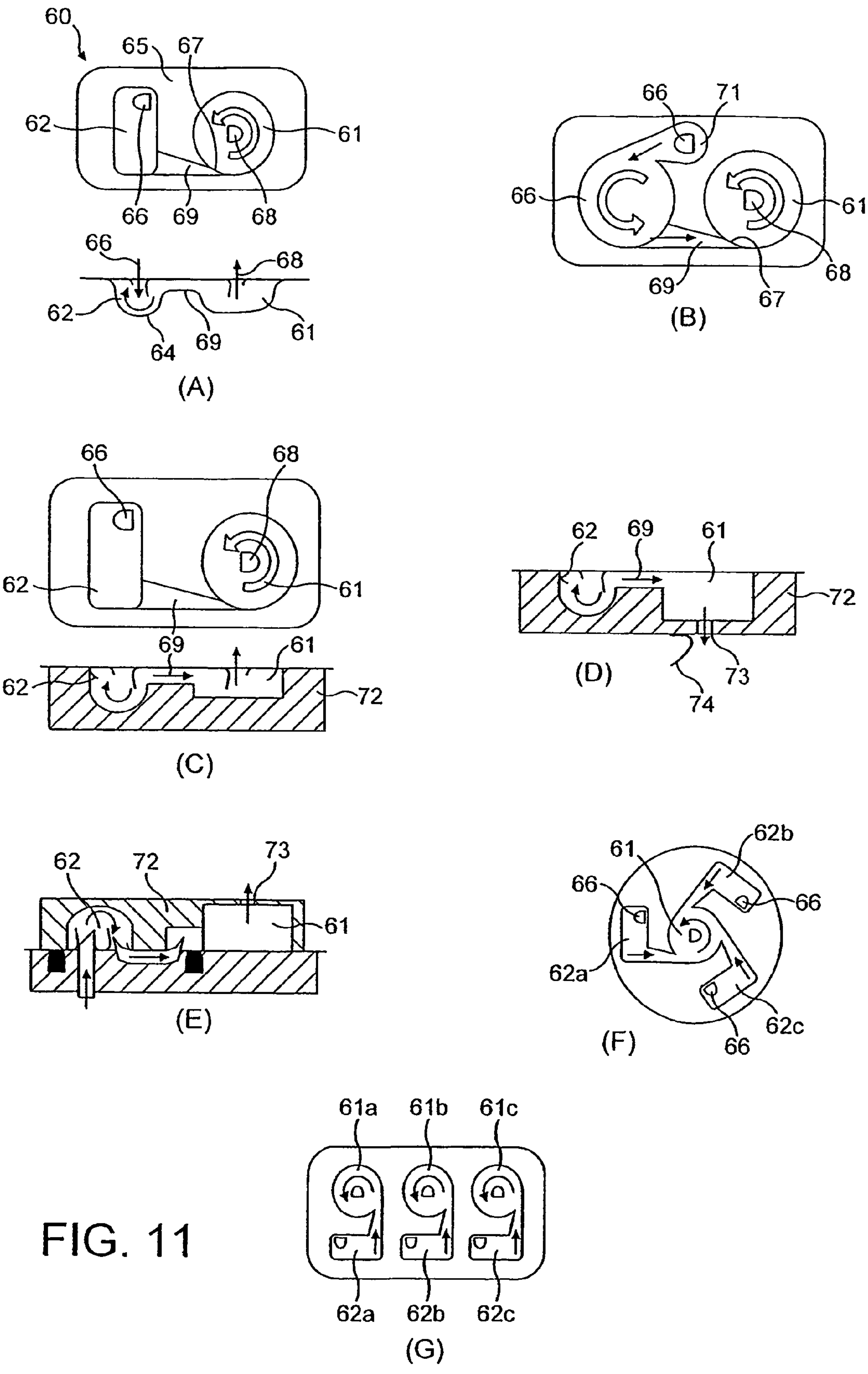

Table 7 shows the results obtained when the embodiment of FIG. 2 is tested with the secondary piercing member used in FIG. 11 and, when the embodiment of FIG. 11 is used with the secondary piercing element of FIG. 3. This shows that the best performance is obtained when the tangential airflow inlet to the plenum chamber 22 is combined with the secondary piercing element of FIG. 11.

TABLE 7

Effect of inhaler orientation with combinations of standard and swirl piercing arrangements.

| Standard plenum (as in FIG. 2) with secondary piercing element of FIG. 6 | | | | Tangential inlet to plenum (as in FIG. 7) with secondary piercing element of FIG. 2) | | | |
|---|---|---|---|---|---|---|---|
| Correct pierce orientation | | Pierced upside down | | Correct pierce orientation | | Pierced upside down | |
| Mean ED: | 78% | Mean ED: | 83% | Mean ED: | 89% | Mean ED: | 87% |
| RSD: | 12% | RSD: | 8% | RSD: | 7% | RSD: | 10% |

It has also been found that with a vortex nozzle aerosolising system it is desirable that the maximum loading of powder going through the nozzle (i.e. mass of powder per second) is kept below a threshold. Above this threshold the nozzle can become overloaded and its efficiency is reduced and this has a detrimental effect on the delivered dose. It is therefore desirable to spread out the introduction of the powder to the nozzle over a period of time so that the powder density in the nozzle is kept sufficiently low to maintain the nozzle's efficiency.

A further benefit of generating swirl in the blister is that the time over which the powder is entrained in the airflow is increased, thus helping to achieve a more even flow of powder into the aerosolising nozzle.

Figure 7C:
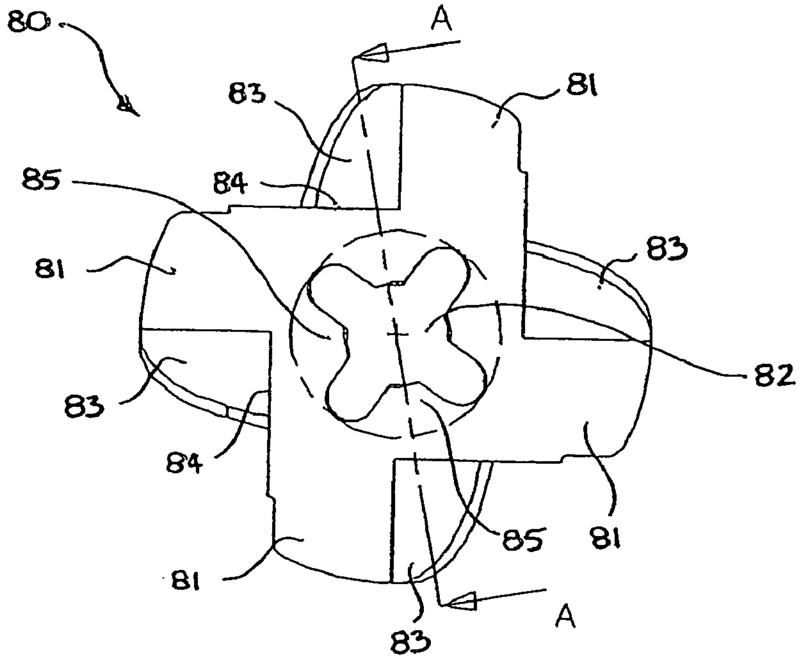
FIGS. 7C and 7D illustrates a top plan view and a cross-sectional view along line A-A, respectively, of a modified piercing element according to an embodiment of the invention.
Figure 7D:
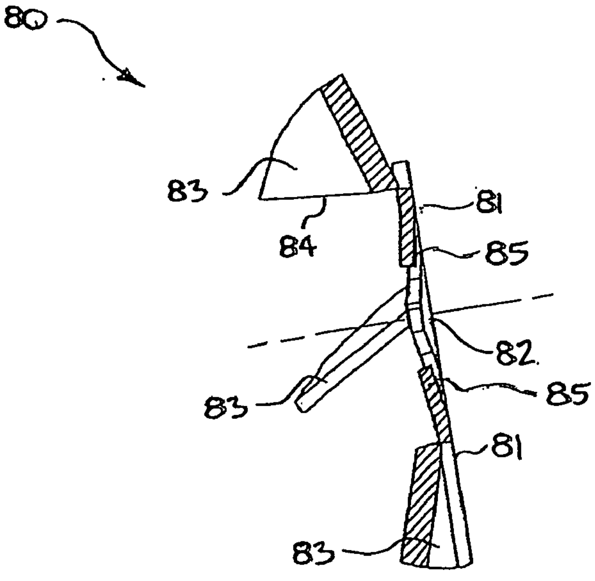
Figure 8:
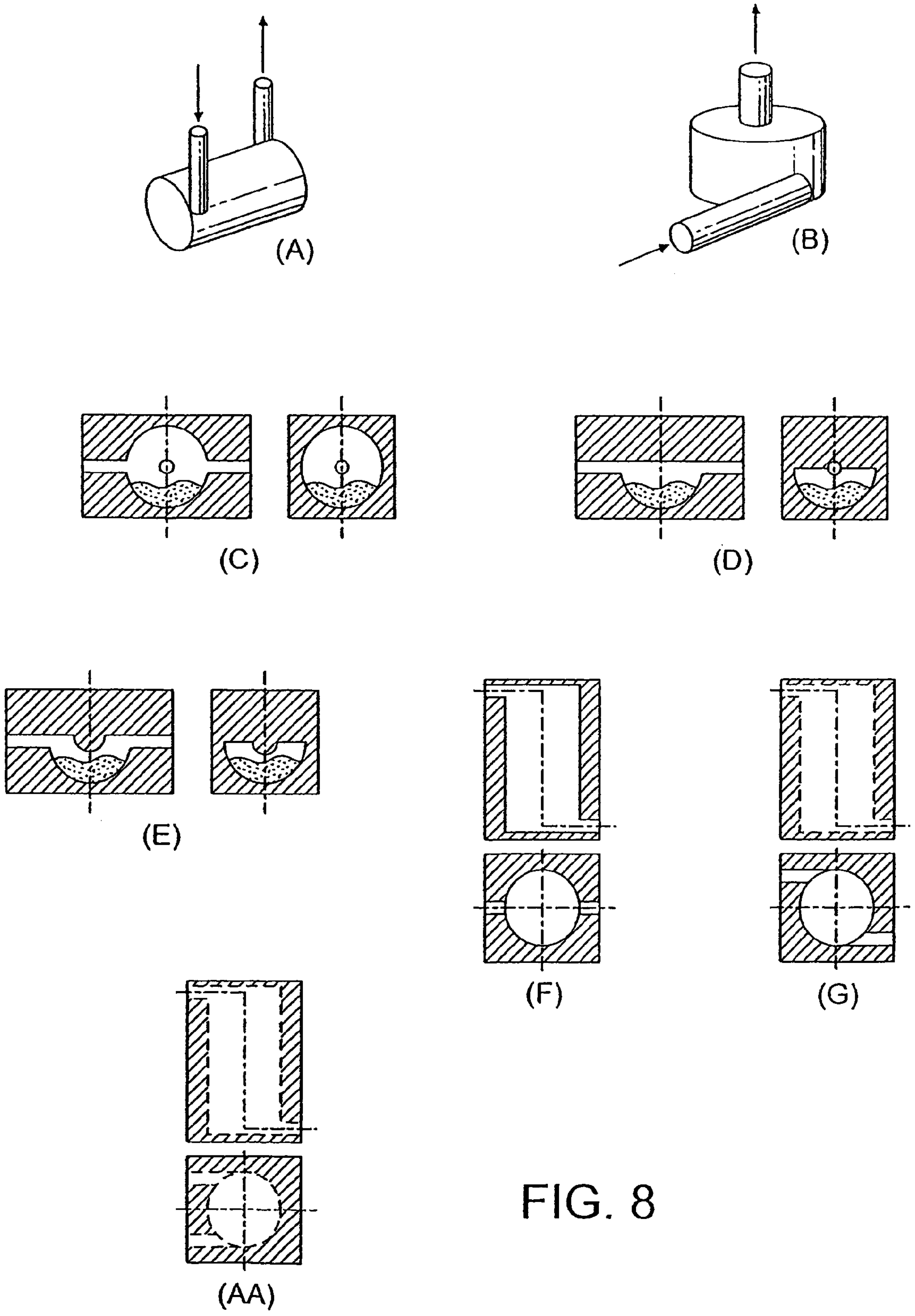
FIG. 8A to 8G illustrate various versions of medicament packs which promote the entrainment and evacuation of the dose therefrom.

A modified version of the piercing member 35 of FIGS. 6A and 6B is illustrated in FIGS. 7C and 7D. The piercing member 80 of this embodiment also comprises four blades 81 extending radially from a central aperture 82. A vane 83 depends at an angle of 40 degrees to the axis of piercing from each blade 81. It will be noted that, in this embodiment, the vanes 82 are wider and so have a greater surface area because there is no gap between the inner edge 84 of each vane 82 and the edge of an adjacent blade 81, as there is in the embodiment of FIG. 6A. The larger surface area of the vanes 82 assists in promoting swirl to a greater extent within the blister and cuts a larger opening in the blister without increasing the overall size of the piercing element.

The piercing member 80 is mounted on the central feed tube 23 using a "starlock" feature. As can be seen in FIGS. 7C and 7D, four prongs 85 protrude into the central aperture 82 and are slightly deflected out of the plane of the blades 81. The central feed tube 23 is forced through the central aperture 82 to further deflect the prongs 85 out of the plane of the blades 81 to attach the piercing member 80 to the central feed tube 23 and achieve consistent positioning on the central feed tube 23. The deflected prongs 85 grip the outside of the central feed tube 23 and prevent removal of the piercing member 80 therefrom. Although four prongs 85 are shown in FIGS. 7C and 7D, it will be appreciated that 2 or more prongs 85 may be employed. However, preferably between 4 and 8 prongs 85 are used in practice.

The preferred dimensions and angles for the piercing member 80 of the embodiment shown in FIGS. 7C and 7D are listed in Table 5A. Reference should again be made to FIG. 6C for identification of the dimensions and angles given in Table 5A.

TABLE 5A

Preferred dimensions for the secondary piercing element of FIGS. 7C and 7D.

| Dimension | Description | Value |
|---|---|---|
| B | Span of piercing element | 7.2 mm |
| w | Width of piercing vanes | 1.8 mm |
| s | Height of piercing element | 2.1 mm |
| β | Angle of vanes to the axis of piercing | 40° |
| $D_0$ | Plenum diameter | 6.8 mm |
| $D_1$ | Plenum inner diameter | 3.8 mm |
| f | Plenum inlet height | 1.5 mm |
| g | Plenum inlet width | 1.5 mm |
| H | Plenum height | 3.75 mm |

As with the embodiment of FIGS. 6A and 6B, the piercing element 80 is formed from sheet material by mechanical punching and pressing. A chemical or electrochemical etching process can also be used to cut out the "blanks" prior to forming.

Referring to the dimensions marked on FIG. 4, the preferred values for the dimensions of the blister are shown in Table 5B below. The blister bowl is a half elipse in section and circular in shape when viewed from above the bowl.

TABLE 5B

Preferred dimensions for blister.

| Dimension | Description | Value |
|---|---|---|
| C | Major axis of eliptical section (without fillet radius) | 8.0 mm |
| E | Depth of eliptical section (=half minor axis of elipse) | 2.8 mm |
| Z | Fillet radius at root of blister bowl | 0.5 mm |

Improved Medicament Pack

In addition to providing devices which enhances the evacuation of the drug from a conventional blister 12, the inventors have also developed a new type of medicament pack for storage of a drug dose especially for use with a dry powder inhaler which is designed to minimise restriction to the gas flow from the pressurised gas source to the aerosolising nozzle as well as generate a swirling air flow between the air inlet and outlet to the packaging so as to entrain the drug and evacuate substantially all of the drug from the pack.

Figure 10:
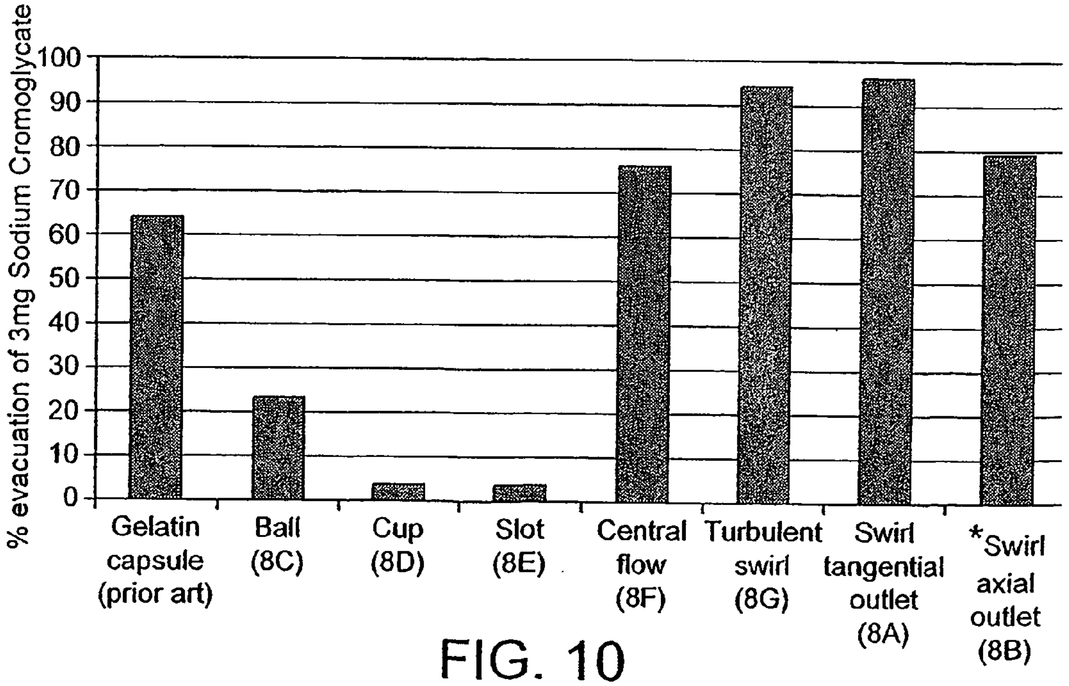
FIG. 10 is a table to illustrate the performance of some of the medicament packs shown in FIGS. 8A to 8G, and FIG. 11A to 11G illustrate various medicament packs incorporating a aerosolising nozzle according to the invention.

Two preferred embodiments of medicament pack according to the invention are illustrated in FIGS. 8A and 8B. FIG. 10 is a table showing the percentage of drug (3 mg Sodium Cromoglycate—the entrainment device was attached to airflow control apparatus set up to deliver a flow rate of 2 lpm for a period of 3 seconds, apart from the embodiment of FIG. 8B which was tested at 3 lpm) evacuated using each of these chamber designs together with the results obtained using a number of other packages illustrated in the cross sectional views of FIGS. 8C to 8G, as well as a conventional gelatin capsule, for comparison purposes.

As can be seen, the inventors have found that very efficient entrainment of dry powder is obtained when the dose is contained in a cylindrical swirl chamber 45 having facing opposite end walls and a tangential inlet 46 and outlet 47, the inlet 46 and outlet 47 being situated at opposite ends of the swirl chamber 45, as shown in the embodiment of FIGS. 8A and 8AA showing a perspective view, and two cross-sectional views, respectively. Preferably, the chamber diameter is 4 mm and the its length is 7 mm.

Slightly less efficient entrainment is obtained when the dose is contained in a cylindrical swirl chamber 48 provided with a tangential inlet 49 and an outlet 50 coaxial with the longitudinal axis of the chamber, as shown in the perspective view of FIG. 8B.

When one of the aforementioned medicament packs are used, the outlet of the swirl chamber 47,50 is connected to an aerosolising nozzle and the swirl chamber inlet 46,49 is connected to a valve which is in turn connected to a source of pressurised gas. In use, when the valve is opened, for example, in response to the user's inhalation, a charge of pressurised gas flows into the chamber 45,48 creating a swirling flow from the inlet 46,49 to the outlet 47,50, due to the shape of the chamber 45,48, which scours a very high proportion of the dry powder dose and delivers it through the outlet 47,50 to the aerosolising nozzle.

Figure 9:
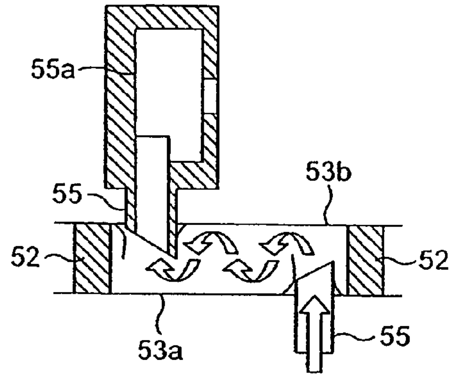
FIG. 9 illustrates another embodiment of blister pack for containing a dose of medicament for use in an inhaler.

Another embodiment of medicament pack according to the invention is illustrated in the cross-sectional view of FIG. 9. As can be seen, the pack 51 comprises a plastic moulded housing 52 in the form of a short tube with open ends. A piercable foil laminate 53*a*, 53*b* seals each open end. When the pack 51 is to be used, the foil 53*a* is pierced to allow an airflow inlet tube 54 to penetrate into the pack 51 and the foils 53*b* is pierced to allow a drug outlet tube 55 which communicates with an aerosolising nozzle 55*a* to penetrate into the pack. The foils 53*a*, 53*b* are pierced such that the air must pass substantially through the whole of the pack before it reaches the outlet so that the dose contained therein is entrained in the airflow. This type of pack may be used with a number of inhalers each having a different design as the pack can be pierced on both sides or, just on one side as with a conventional blister pack.

As previously mentioned, any deposition of drug within the device can have a significant effect on the variation of the delivered dose in successive uses of the device as well as on the fine particle fraction of total dose. Therefore, it is desirable to minimise the components of the device with which the drug entrained in the airflow can come into contact. To this end, the present invention also provides a medicament pack in which the drug storage chamber, the aerosolising nozzle and the drug feed tube between the nozzle and the blister are formed together in a single use integrated module that is discarded after each time the device is used. FIGS. 11A to 11G illustrate various embodiments of drug packages incorporating one or more aerosolising nozzles according to the invention. A preferred embodiment of pack 60 is illustrated in FIG. 11A in which the aerosolising nozzle 61 and the dose storage blister 62 are both formed from a cold formed foil base 64 covered with a puncturable lidding foil 65. The lid 65 is sealed to the base 64 preferably by heat sealing. The dose storage chamber 62 may be shaped as a half cylinder so as to promote the swirling flow of air as it enters via an inlet 66 formed therein as a result of piercing the lidding foil 65. The other chamber 61 may be configured as a nozzle or vortex chamber with a tangential inlet 67 and a central axial outlet 68 which is also formed by piercing the lid 65. When a charge of pressurised gas is passed into the drug storage chamber 62 via the inlet 66, the dose contained in the chamber 62 is entrained in the airflow. The entrained dose flows into the nozzle 61 via an intermediate conduit 69 between the drug storage chamber 62 and the nozzle 61 where the dose is aetosolised by the action of shear forces, turbulence and impaction. The aerosolised dose leaves the nozzle 61 via the outlet port 68. Preferably, the diameter of the nozzle 61 is 8 mm and its depth is in the range 1.0 to 2.8 mm.

A modified version of the preferred embodiment of FIG. 11A is illustrated in FIG. 11B. In this arrangement, the dose storage chamber 66 is cylindrical in shape has a tangential inlet 70 from an additional inlet cavity in which the inlet 66 is pierced by the inhaler.

Another embodiment is illustrated in FIG. 11C. Instead of forming the dose storage chamber 62 and aerosolising nozzle 61 from foil using cold forming, the dose storage chamber 62 and nozzle 61 are formed from a plastic moulding 72 onto which the lid 65 is sealed, as with the embodiments of FIGS. 11A and 11B. The advantage of moulding the nozzle 61 and dose storage chamber 62 allows greater accuracy and definition to be achieved in the geometry of the chambers 61,62 than is achievable when the dose storage chamber 62 and nozzle 61 is formed entirely of foil.

FIG. 11D shows a modified version of the combined dose storage chamber 62 and nozzle 61 of FIG. 11C. Instead of forming the outlet 68 from the nozzle 61 in the lidding foil 65, an outlet 73 is formed in the moulded plastic component which may be sealed with a foil flap 74 prior to use and which is pealed away to open the outlet 73. This improves the definition achievable in the geometry of the outlet 73.

Another embodiment is illustrated in FIG. 11E. In this version, there is no intermediary conduit 69 between the drug storage chamber 62 and the nozzle 61. Instead, this is formed in the inhaler which pierces an outlet 75 for the drug in the foil covering the drug storage chamber 62 in addition to the inlet 66. The inhaler must also pierce an opening in the lid 65 covering the nozzle 61 to form an inlet for the compressed air together with the drug entrained therein. The outlet 73 may be formed in the plastic moulding as described with reference to FIG. 11D. The advantage of this arrangement is that the powder is contained in the dose storage chamber 62 and cannot migrate into the vortex chamber 61 until the lid 65 is pierced when the pack is used.

Further arrangements are shown in FIGS. 11F and 11G. In the embodiment of FIG. 11F, multiple drug storage chambers 62 are shown which feed a single aerosolising nozzle 61. It will be appreciated that this embodiment is not as efficient as those which embody a single use nozzle as deposition of drug may occur during, for example, evacuation of the first dose storage chamber 62*a*, which will have an affect on the delivered dose when the second and/or third dose storage chambers 62*b*, 62*c* are used together with the same nozzle 61. FIG. 11G illustrates multiple dose storage 62*a*, 62*b*, 62*c* and nozzle 61*a*, 61*b*, 61*c* pairs in a single assembly. Preferably, the dose storage and vortex chambers are formed from cold formed foil covered with piercable lidding foil.

Many modifications and variations of the invention falling within the terms of the appended claims will be apparent to those skilled in the art and the foregoing description should be regarded as a description of the preferred embodiments only. In particular, although the embodiments described herein refer primarily to active, i.e. powered, dry powder dispersion inhalers, the concepts apply equally to passive dry powder inhalers where the dispersion energy is provided by the user of the device. As will be appreciated by a skilled person, the dimensions of the air pathways through the entrainment blister or chamber and the aerosolising nozzle would need to be enlarged in order to provide a sufficiently low pressure drop for passive inhalation. For example, this could be achieved by scaling up the size of the device in proportion.

The invention claimed is:

1. A dry powder inhaler for delivering a dose of medicament for inhalation by a user, the dose being contained in a medicament pack having an interior and a puncturable lid, the inhaler comprising a drug entrainment device including a drug outlet tube terminating with a primary piercing element to pierce an opening in said lid when the medicament pack is located in the inhaler, a secondary piercing member to pierce a plurality of peripheral openings in said lid and, an airflow path to enable the supply of a charge of gas into the medicament pack via said peripheral openings to scour the interior of the pierced medicament pack such that substantially all of the dose is entrained in the gas and flows out of the medicament pack via the drug outlet tube, wherein the secondary piercing member comprises a plurality of blades with a vane depending from each blade that extend towards and pierces the lid of a pack to direct a swirling flow of air therein, the vanes having arcuately shaped outer edges.

2. An inhaler according to claim 1, wherein the drug outlet tube is in communication with an aerosolizing device, the aerosolizing device arranged to aerosolize the dose entrained in the gas for inhalation by a user.

3. An inhaler according to claim 2, wherein said aerosolizing device includes a nozzle having a substantially circular cross-section with a substantially tangential inlet port from the drug feed tube and substantially axial exit port.

4. An inhaler according to claim 1, wherein the airflow path comprises an annular conduit in the drug entrainment device that surrounds the drug outlet tube.

5. An inhaler according to claim 1, wherein the drug entrainment device includes an airflow inlet for the flow of air from the airflow path into a plenum chamber formed in a space between the drug entrainment device and a lid of a pierced medicament pack mounted in the inhaler, the inlet and the plenum chamber being configured such that a swirling airflow is generated in the plenum chamber above the lid of the pierced medicament pack.

6. An inhaler according to claim 5, wherein the plenum chamber is substantially cylindrical in shape and has a curved wall, the inlet intersects the curved wall of the chamber at a tangent thereto such that the air flows into the plenum chamber in a direction substantially parallel to the lid of the pierced medicament pack.

7. An inhaler according to claim 4-5, wherein the drug entrainment device further comprises a housing and the secondary piercing member protrudes from an end face of said housing such that said end face forms a seal around the periphery of the lid of the medicament pack when said primary piercing element and secondary piercing member pierce said lid.

8. An inhaler according to claim 7, wherein said plenum chamber is partially formed from a recess in said end face.

9. An inhaler according to claim 1, wherein the secondary piercing member is mounted on the drug outlet tube.

10. An inhaler according to claim 1, wherein the secondary piercing member is configured to form a substantially circular pattern or ring of openings in the lid of the medicament pack.

11. An inhaler according to claim 10, wherein the secondary piercing member comprises an annulus with a plurality of cutting teeth depending from the periphery thereof.

12. An inhaler according to claim 11, wherein each tooth has two cutting edges of equal length that converge towards a pointed tip.

13. An inhaler according to claim 12, wherein the cutting teeth are angled away from the axis of the annulus by an angle of between 30 and 60 degrees.

14. An inhaler according to claim 13, wherein the secondary piercing member is formed from a sheet of material and the teeth are bent out of the plane of the sheet.

15. An inhaler according to claim 5, wherein the secondary piercing member is configured to direct the swirling flow of air in the plenum chamber into the medicament pack through the openings formed therein by the secondary piercing member.

16. An inhaler according to claim 1, wherein the blades are located substantially parallel to the lid of the medicament pack that has been pierced and the vanes are deflected out of the plane of the blades towards and into the medicament pack.

17. An inhaler according to claim 15, wherein the secondary piercing member is mounted on the drug outlet tube, the axis of the drug outlet tube being substantially at right angles to the airflow inlet to the plenum chamber such that the airflow generated in the plenum chamber and the medicament pack swirls substantially about the axis of the drug outlet tube.

18. An inhaler according to claim 1, further comprising a medicament pack containing a dose of powdered medicament mountable therein for inhalation by a user using the inhaler, the medicament pack comprising a circular blister having a piercable lid.

19. An inhaler according to claim 18, wherein the drug entrainment device and the lid of the blister together define the walls of a substantially cylindrically shaped plenum chamber when the blister is pierced by the drug entrainment device, the plenum chamber including an inlet in communication with the airflow path to enable the supply of a charge of gas into the medicament pack via the plenum chamber and the peripheral openings in the lid, wherein the inlet is configured such that the air flows into the plenum chamber in a direction substantially parallel to the surface of the lid.

20. An inhaler according to claim 19, wherein the inlet intersects the cylindrical wall of the plenum chamber at a tangent to generate a swirling airflow in the plenum chamber.

* * * * *

UNITED STATES PATENT AND TRADEMARK OFFICE

CERTIFICATE OF CORRECTION

PATENT NO. : 7,810,494 B2
APPLICATION NO. : 10/571725
DATED : October 12, 2010
INVENTOR(S) : Quentin Harmer et al.

It is certified that error appears in the above-identified patent and that said Letters Patent is hereby corrected as shown below:

On the cover page, item (73) the Assignee should be listed as Vectura Delivery Devices Limited Signed and Sealed this
Twelfth Day of July, 2011

David J. Kappos
*Director of the United States Patent and Trademark Office*